United States Patent
Kiyose et al.

(10) Patent No.: US 10,517,566 B2
(45) Date of Patent: Dec. 31, 2019

(54) ULTRASONIC DEVICE, ULTRASONIC PROBE, ELECTRONIC EQUIPMENT, AND ULTRASONIC IMAGE DEVICE

(71) Applicant: SEIKO EPSON CORPORATION, Tokyo (JP)

(72) Inventors: Kanechika Kiyose, Nagano (JP); Hironori Suzuki, Nagano (JP); Hiroshi Matsuda, Gifu (JP)

(73) Assignee: Seiko Epson Corporation, Tokyo (JP)

(*) Notice: Subject to any disclaimer, the term of this patent is extended or adjusted under 35 U.S.C. 154(b) by 505 days.

(21) Appl. No.: 14/499,806

(22) Filed: Sep. 29, 2014

(65) Prior Publication Data
US 2015/0094596 A1   Apr. 2, 2015

(30) Foreign Application Priority Data
Sep. 30, 2013   (JP) .................. 2013-203475

(51) Int. Cl.
*A61B 8/00* (2006.01)
*G10K 11/30* (2006.01)

(52) U.S. Cl.
CPC ............ *A61B 8/4427* (2013.01); *G10K 11/30* (2013.01); *A61B 8/461* (2013.01)

(58) Field of Classification Search
CPC ..... A61B 8/4427; A61B 8/4483; A61B 8/445; A61B 8/461; B06B 1/0629;
(Continued)

(56) References Cited

U.S. PATENT DOCUMENTS

| 4,862,893 A * | 9/1989 | Martinelli ............ A61B 8/0833 600/459 |
| 5,886,454 A * | 3/1999 | Ito .................. B06B 1/0622 310/322 |

(Continued)

FOREIGN PATENT DOCUMENTS

| JP | 2005-051688 A | 2/2005 |
| JP | 2007-235795 A | 9/2007 |

(Continued)

OTHER PUBLICATIONS

"Ultrasonic data values for plastics". Signal Processing. Accessed Feb. 8, 2017. http://www.signal-processing.com/us_data_p.html.*

(Continued)

*Primary Examiner* — Angela M Hoffa
*Assistant Examiner* — Helene Bor
(74) *Attorney, Agent, or Firm* — Global IP Counselors, LLP

(57) ABSTRACT

An ultrasonic device includes a base, a plurality of ultrasonic transducer elements, an acoustic adjustment layer, and a wall part. The ultrasonic transducer elements are arranged in an array form on the base, each of the ultrasonic transducer elements having a vibration film. The acoustic adjustment layer is disposed on each of the ultrasonic transducer elements. The wall part is arranged between adjacent ones of the ultrasonic transducer elements when viewed in a plan view along a thickness direction of the base such that the acoustic adjustment layer on the adjacent ones of the ultrasonic transducer elements are separated by the wall part in a range of at least a portion of a height of the acoustic adjustment layer measured from the base. The wall part has an acoustic impedance that is higher than an acoustic impedance of the acoustic adjustment layer.

8 Claims, 10 Drawing Sheets

(58) Field of Classification Search
CPC ... B06B 2201/76; B06B 1/0292; G10K 11/30; G10K 9/12; Y10T 29/49005
See application file for complete search history.

(56) References Cited

U.S. PATENT DOCUMENTS

| | | | |
|---|---|---|---|
| 6,225,729 | B1 | 5/2001 | Izumi et al. |
| 2006/0238067 | A1* | 10/2006 | Dausch ................ B06B 1/0622 310/311 |
| 2007/0164632 | A1* | 7/2007 | Adachi ................ A61B 8/4483 310/311 |
| 2007/0299345 | A1* | 12/2007 | Adachi .................... A61B 8/12 600/459 |
| 2008/0284287 | A1 | 11/2008 | Yoshimura et al. |
| 2011/0115337 | A1* | 5/2011 | Nakamura ............. G10K 9/122 310/334 |
| 2012/0187508 | A1* | 7/2012 | Adler ................... B06B 1/0292 257/416 |
| 2012/0247217 | A1* | 10/2012 | Suzuki .................. B25J 13/082 73/717 |
| 2013/0338507 | A1 | 12/2013 | Onishi et al. |

FOREIGN PATENT DOCUMENTS

| | | |
|---|---|---|
| JP | 2008-283618 A | 11/2008 |
| JP | 2011-099675 A | 5/2011 |
| JP | 2012-215533 A | 11/2012 |
| JP | 103240220 A | 8/2013 |
| JP | 2013-255692 A | 12/2013 |

OTHER PUBLICATIONS

Fracno et al. "Determination of the acoustic properties of tungsten/epoxy and tungsten/polyurethane composites using utlrasonic transmission techique". Proceedings of COBEM 2005. 18th International Congress of Mechanical Engineering. Nov. 6-11, 2005.*

* cited by examiner

ULTRASONIC DEVICE, ULTRASONIC PROBE, ELECTRONIC EQUIPMENT, AND ULTRASONIC IMAGE DEVICE

CROSS-REFERENCE TO RELATED APPLICATIONS

This application claims priority to Japanese Patent Application No. 2013-203475 filed on Sep. 30, 2013. The entire disclosure of Japanese Patent Application No. 2013-203475 is hereby incorporated herein by reference.

BACKGROUND

Technical Field

The present invention relates to an ultrasonic device, ultrasonic probe, electronic equipment, and ultrasonic image device or the like using the same.

Related Art

Ultrasonic devices are generally known. For example, with the ultrasonic device noted in Japanese Laid-Open Patent Publication No. 2005-51688, a plurality of ultrasonic transducer elements are arranged in array form. The ultrasonic transducer elements have a vibration film. A piezoelectric body and electrode are formed on the vibration film. Ultrasonic waves are emitted according to the ultrasonic vibration of the vibration film.

SUMMARY

If an acoustic adjustment layer is adhered and overlapped on the vibration film of the ultrasonic device, interposition of an air layer is avoided, and ultrasonic waves are transmitted efficiently. For example, as noted in Japanese Laid-Open Publication No. 2007-235795, with so-called bulk ultrasonic transducer elements, proposed is an acoustic adjustment layer adhered to the surface of a bulk piezoelectric body. The acoustic adjustment layer is segmented for each individual piezoelectric body. Packing material is packed between adjacent acoustic adjustment pieces. The acoustic impedance of the packing material is lower than the acoustic impedance of the acoustic adjustment body. The packing material has the role of preventing crosstalk between adjacent acoustic adjustment pieces. However, in contrast to bulk piezoelectric bodies, since the acoustic impedance of the acoustic adjustment layer is low, there is a demand for the acoustic impedance of the acoustic adjustment layer adhered to the vibration film to be low. With Japanese Laid-Open Publication No. 2007-235795, the acoustic impedance of the packing material has to be lower than the acoustic impedance of the acoustic adjustment layer, so with an ultrasonic device using a vibration film, it was difficult to select a material for the packing material, and as a result, it was difficult to segment the acoustic adjustment layer adhered to the vibration film.

With at least one aspect of the present invention, it is possible to provide an ultrasonic device having an acoustic adjustment layer for which it is possible to prevent crosstalk well while adhering to the vibration film.

(1) An ultrasonic device according to one aspect includes a base, a plurality of ultrasonic transducer elements, an acoustic adjustment layer, and a wall part. The ultrasonic transducer elements are arranged in an array form on the base, each of the ultrasonic transducer elements having a vibration film. The acoustic adjustment layer is disposed on each of the ultrasonic transducer elements. The wall part is arranged between adjacent ones of the ultrasonic transducer elements when viewed in a plan view along a thickness direction of the base such that the acoustic adjustment layer on the adjacent ones of the ultrasonic transducer elements are separated by the wall part in a range of at least a portion of a height of the acoustic adjustment layer measured from the base. The wall part has an acoustic impedance that is higher than an acoustic impedance of the acoustic adjustment layer.

When sending ultrasonic waves, the vibration film of the ultrasonic transducer element does ultrasonic vibration. The ultrasonic vibration propagates within the acoustic adjustment layer, and is emitted from the interface of the acoustic adjustment layer. At this time, a wall part having greater acoustic impedance than the acoustic impedance of the acoustic adjustment layer is arranged between the adjacent ultrasonic transducer elements. In this way, an interface is formed on the acoustic adjustment layer between ultrasonic transducer elements according to the difference in acoustic impedance. The interface prevents transmission of the ultrasonic vibration. As a result, transmission of ultrasonic vibration from one vibration film that is doing ultrasonic vibration toward the vibration films of adjacent ultrasonic transducer elements is prevented. Ultrasonic wave crosstalk is prevented during ultrasonic vibration of one vibration film.

(2) The wall part is preferably made of a material having larger Young's modulus than Young's modulus of a material of the acoustic adjustment layer. The rigidity of the acoustic adjustment layer is reinforced by the wall part. Crushing of the acoustic adjustment layer in the thickness direction is prevented. The distance between the vibration film and the interface is kept constant. As a result, it is possible to have ultrasonic waves be radiated from the interface efficiently.

(3) The ultrasonic device preferably further includes an acoustic lens adhered the acoustic adjustment layer. The acoustic lens is preferably bonded to a top surface of the wall part using an adhesive layer. The acoustic adjustment layer functions as an adhesive agent. Though the acoustic adjustment layer is interrupted by the wall part, the acoustic lens is adhered to the wall part by the work of the adhesive layer. Even when the wall part is formed, a reduction in the acoustic lens adherence area is kept to a minimum. In fact, when the acoustic lens is bonded to the wall part, it is possible for the acoustic lens and the wall part to form a structure. The structure can even more reliably prevent deformation of the acoustic adjustment layer.

(4) The wall part preferably has a cavity recessed from a bonding surface with the acoustic lens, and the cavity is filled with the adhesive layer. The acoustic lens is received on the bonding surface of the wall part. Therefore, the thickness of the acoustic adjustment layer is determined by the position of the bonding surface of the wall part. It is possible to set the thickness of the acoustic adjustment layer with good precision according to the dimensional precision of the wall part. In fact, the reduction of the acoustic lens adhesion area is kept to a minimum.

(5) The adhesive layer is preferably made of the same material as the acoustic adjustment layer. It is possible to form the adhesive layer with the same manufacturing process as that of the acoustic adjustment layer. This avoids having the manufacturing process become complex. An increase in manufacturing costs is avoided.

(6) The wall part preferably separates the acoustic adjustment layer for each of an ultrasonic transducer element group including the ultrasonic transducer elements connected in common to one signal line among the ultrasonic transducer elements. Vibration films belonging to the ultrasonic transducer element group connected in common to one signal line vibrate simultaneously according to the supply of drive signals. The transmission of ultrasonic vibration from these vibration films toward vibration films belonging to other ultrasonic transducer element groups is prevented.

(7) The wall part preferably separates the acoustic adjustment layer on the adjacent ones of the ultrasonic transducer elements within the ultrasonic transducer element group. The transmission of ultrasonic vibration between simultaneously vibrating vibration films is prevented. Ultrasonic wave crosstalk between vibration films vibrating simultaneously is prevented.

(8) The ultrasonic device can be used incorporated in a probe. It is possible for the probe to be equipped with the ultrasonic device, and a case supporting the ultrasonic device.

(9) The ultrasonic device can be used incorporated in an electronic equipment. It is possible for the electronic equipment to be equipped with the ultrasonic device, and a processing device connected to the ultrasonic device, and configured to process the output of the ultrasonic device.

(10) The ultrasonic device can be used incorporated in an ultrasonic image device. It is possible for the ultrasonic image device to be equipped with the ultrasonic device, and a display device configured to display an image generated based on the output of the ultrasonic device.

BRIEF DESCRIPTION OF THE DRAWINGS

Referring now to the attached drawings which form a part of this original disclosure.

DETAILED DESCRIPTION OF EXEMPLARY EMBODIMENTS

Hereafter, an embodiment of the present invention while referring to the attached drawings will be described. This embodiment described hereafter does not unduly limit the contents of the present invention noted in the scope of patent claims, and all of the structures described with this embodiment are not absolutely necessary as means for solving of the present invention.

(1) Overall Configuration of the Ultrasonic Diagnostic Device

Figure 1:
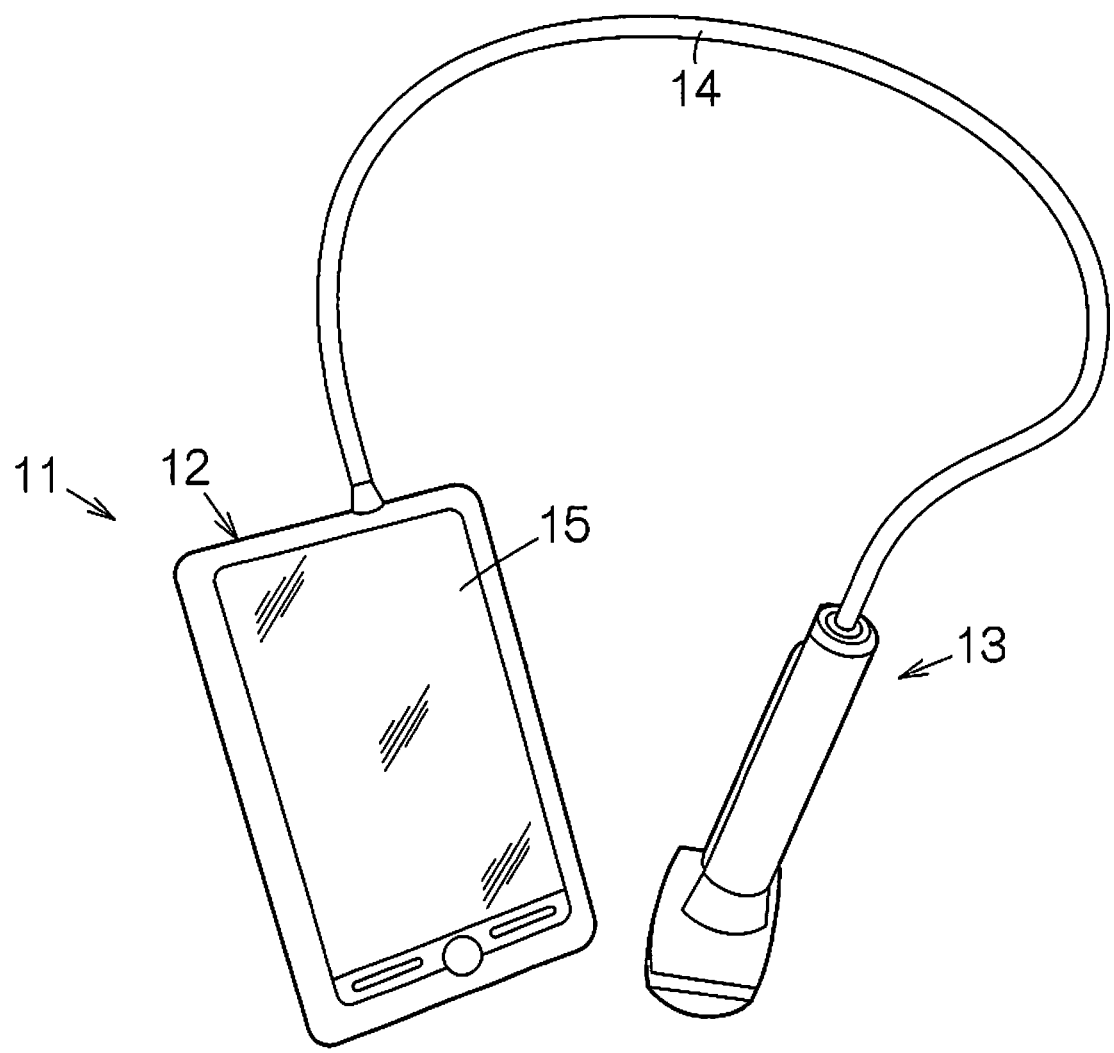
FIG. 1 is an external view schematically showing an ultrasonic diagnostic device as an example of electronic equipment.

FIG. 1 schematically shows the configuration of an ultrasonic diagnostic device (ultrasonic image device) 11 as an example of electronic equipment. The ultrasonic diagnostic device 11 is equipped with a device terminal (processing device) 12 and an ultrasonic probe (probe) 13. The device terminal 12 and the ultrasonic probe 13 are connected to each other by a cable 14. The device terminal 12 and the ultrasonic probe 13 exchange electronic signals through the cable 14. A display panel (display device) 15 is incorporated in the device terminal 12. The screen of the display panel 15 is exposed on the surface of the device terminal 12. With the device terminal 12, an image is generated based on the ultrasonic waves detected by the ultrasonic probe 13. The detected results put into image form are displayed on the screen of the display panel 15.

Figure 2:
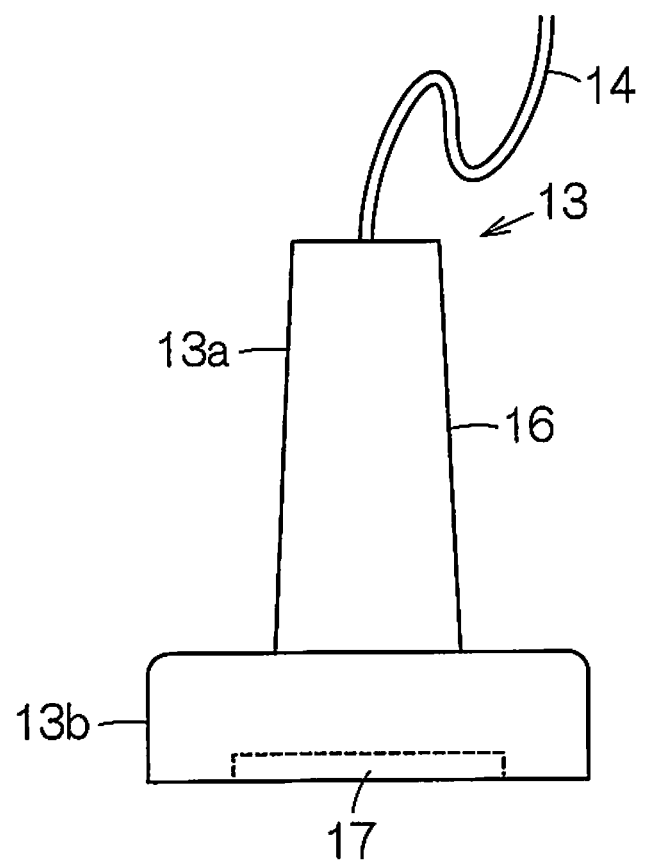
FIG. 2 is an enlarged front view of the ultrasonic probe.

As shown in FIG. 2, the ultrasonic probe 13 has a case 16. Inside the case 16 is housed an ultrasonic transducer element unit (hereafter called "element unit") 17. The surface of the element unit (ultrasonic device) 17 can be exposed on the surface of the case 16. The element unit 17 outputs ultrasonic waves from the surface and receives reflected waves of the ultrasonic waves. In addition, the ultrasonic probe 13 can be equipped with a probe head 13b linked so as to be feely detachable with a probe main unit 13a. At this time, the element unit 17 can be incorporated inside the case 16 of the probe head 13b.

Figure 3:
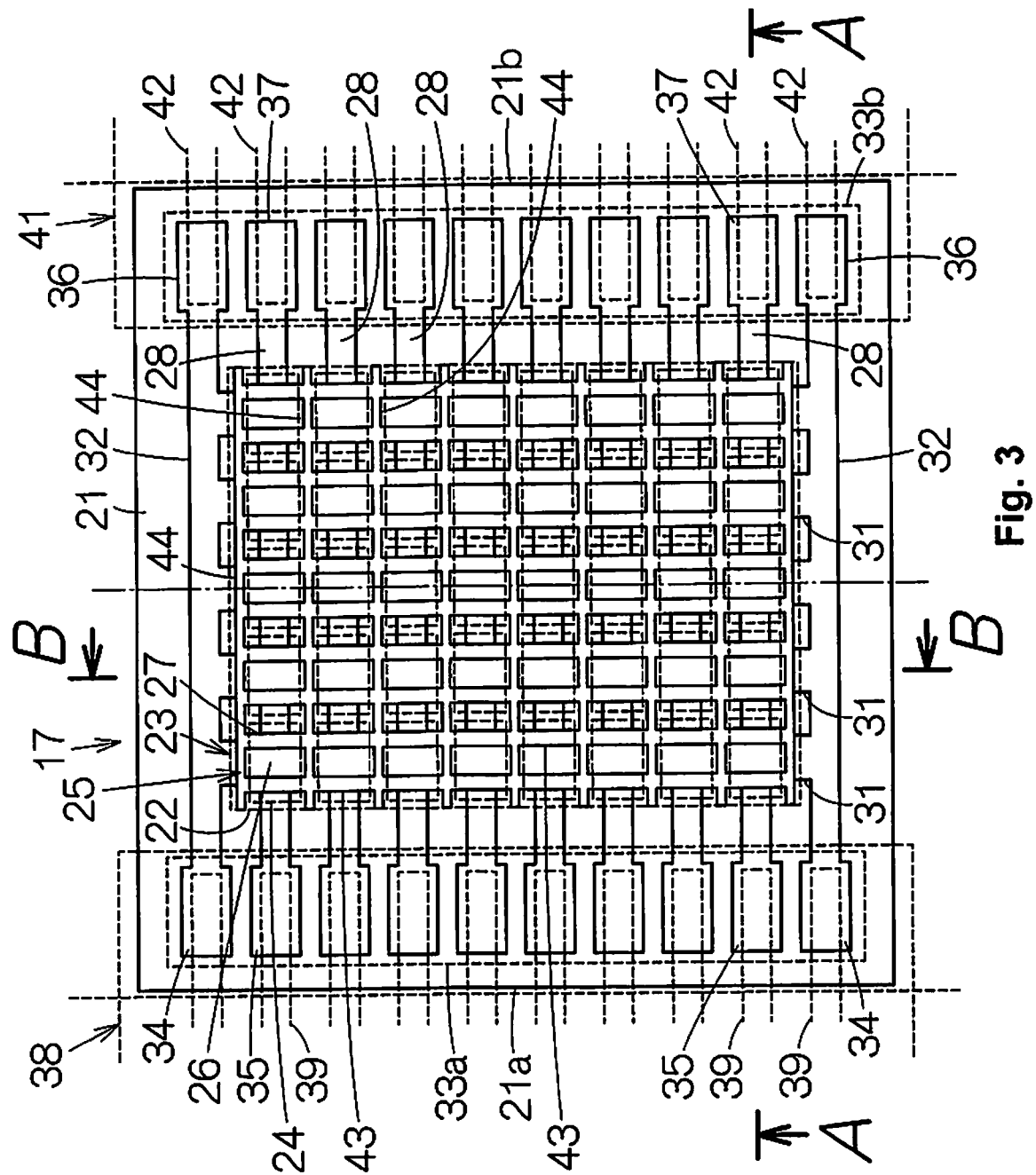
FIG. 3 is an enlarged plan view of the ultrasonic transducer element unit of the first embodiment.

FIG. 3 schematically shows a plan view of the element unit 17 of the first embodiment. The element unit 17 is equipped with a base 21. An element array 22 is formed on the base 21. The element array 22 is constituted with an array of ultrasonic transducer elements (hereafter called "elements") 23. The array is formed in a matrix of a plurality of columns and a plurality of columns. In addition, it is possible to establish a zigzag arrangement for the array. With a zigzag arrangement, the even numbered row element 23 group can be skewed by a column pitch of ½ in relation to the odd numbered Row element 23 group. The number of elements of one of the odd numbered row and the even numbered row can be one less than the number of elements of the other.

Each individual element 23 is equipped with a vibration film 24. Details of the vibration film 24 will be described later. FIG. 3 depicts the outline of the vibration film 24 with a dotted line with a plan view in the direction orthogonal to the film surface of the vibration film 24 (substrate thickness direction plan view). The inner side of the outline correlates to the interior of the area of the vibration film 24. The outside of the outline correlates to outside the area of the vibration film 24. A piezoelectric element 25 is formed on the top of the vibration film 24. As described later, with the piezoelectric element 25, a piezoelectric film (not illustrated) is sandwiched between an upper electrode 26 and a lower electrode 27. These are overlapped in sequence. The element unit 17 is constituted as one ultrasonic transducer element chip.

A plurality of first conductors (signal lines) 28 are formed on the surface of the base 21. The first conductors 28 extend mutually in parallel to the row direction of the array. One first conductor 28 is allocated per row of elements 23. One first conductor 28 is arranged in common with elements 23 aligned in the row direction of the array. The first conductor 28 has the lower electrode 27 formed for each individual element 23. In this way, the first conductor 28 is arranged both inside the area and outside the area of the vibration film 24. For example, titanium (Ti), iridium (Ir), or a laminated film of titanium (Ti) and platinum (Pt) can be can be used for the first conductor 28. However, it is also possible to use other conductive materials for the first conductor 28.

A plurality of second conductors 31 are formed on the surface of the base 21. The second conductors 31 extend mutually in parallel to the column direction of the array. One second conductor 31 is allocated for each column of elements 23. One second conductor 31 is connected in common to elements 23 aligned in the column direction of the array. The second conductor 31 has the upper electrode 26 formed for each individual element 23. Both ends of the second conductor 31 are respectively connected to a pair of lead-out wires 32. The lead-out wires 32 extend mutually in parallel in the row direction of the array. Therefore, all of the second conductors 31 have the same length. In this way, the upper electrodes 26 are connected in common to the elements 23 of the entire matrix. In this way, the second conductors 31 are arranged on the inside area and outside area of the vibration film 24. The second conductors 31 can be formed using iridium (Ir), for example. Other conductors can also be used for the second conductors 31.

The energization of the elements 23 can be switched for each row. Linear scanning or sector scanning is realized according to this energization switching. Since one row of elements 23 output ultrasonic waves simultaneously, it is possible to determine the number of the elements 23 in one row, in other words, the number of columns of the array, according to the ultrasonic wave output level. The number of columns can be set to approximately 10 to 15 columns, for example. This is abbreviated in the drawing with five columns depicted. The number of rows of the array can be determined according to the expansion of the scan range. The number of rows can be set to 128 rows or 256 rows, for example. This is abbreviated in the drawing with eight rows depicted. The role of the upper electrodes 26 and the lower electrodes 27 can also be interchanged. Specifically, while the lower electrodes are connected in common to the elements 23 of the entire matrix, the upper electrodes can be connected in common to each row of the array.

The outline of the base 21 has a first side 21a and a second side 21b facing opposite, partitioned by a pair of straight lines that are mutually parallel. One line of first terminal arrays 33a is arranged between the first side 21a and the element array 22 outline. One line of second terminal arrays 33b is arranged between the second side 21b and the element array 22 outline. The first terminal arrays 33a can be formed in one line in parallel to the first side 21a. The second terminal arrays 33b can be formed in one line in parallel to the second side 21b. The first terminal array 33a is constituted by one pair of upper electrode terminals 34 and a plurality of lower electrode terminals 35. Similarly, the second terminal array 33b is constituted by a pair of upper electrode terminals 36 and a plurality of lower electrode terminals 37. The upper electrode terminals 34 and 36 are respectively connected to both ends of one lead-out wire 32. The lead-out wire 32 and the upper electrode terminals 34 and 36 can be formed plane-symmetrically at the perpendicular plane that bisects the element array 22. The lower electrode terminals 35 and 37 are respectively connected to both ends of one second conductor 31. The second conductor 31 and the lower electrode terminals 35 and 37 can be formed plane-symmetrically at the perpendicular plane that bisects the element array 22. Here, the outline of the base 21 is formed as a rectangle. The outline of the base 21 can also be square or can be a trapezoid.

A first flexible printed wiring board (hereafter called "first wiring board") 38 is coupled to the base 21. The first wiring board 38 is covered by the first terminal array 33a. A conductive line, specifically a first signal line 39, corresponding individually to the upper electrode terminal 34 and the lower electrode terminal 35, is formed on one end of the first wiring board 38. The first signal line 39 is bonded separately facing to individually match the upper electrode terminal 34 and the lower electrode terminal 35. Similarly, a second flexible printed wiring board (hereafter called "second wiring board") 41 is covered on the base 21. The second wiring board 41 is covered by the second terminal array 33b. A conductive line, specifically, a second signal line 42, is formed corresponding individually to the upper electrode terminal 36 and the lower electrode terminal 37 at one end of the second wiring board 41. The second signal line 42 is bonded separately facing to individually match the upper electrode terminal 36 and the lower electrode terminal 37.

An electrode separation film 43 is arranged in parallel with the second conductor 31 on the vibration film 24. The electrode separation film 43 extends in band form in the lengthwise direction of the second conductor 31. The electrode separation film 43 has insulation properties and moisture proof properties. The electrode separation film 43 is formed from a moisture proof insulating material such as alumina ($Al_2O_3$) or silicon oxide ($SiO_2$) for example. The electrode separation film 43 is formed separated at both sides of the second conductor 31 sandwiching each second conductor 31. The second conductor 31 intersects the first conductor 28 on the vibration film 24, so the electrode separation film 43 cuts across the first conductor 28 on the vibration film 24.

A separating wall (wall part) 44 is formed outside the area of the vibration film 24 on the base 21. The separating wall 44 extends in band form in the lengthwise direction of the first conductor 28. The separating wall 44 is arranged between adjacent vibration films 24. The separating wall 44 is formed from a moisture proof insulating material such as alumina, silicon oxide or the like. The raw material of the separating wall 44 can match the raw material of the electrode separation film 43. The separating wall 44 cuts across on the second conductor 31.

Figure 4:
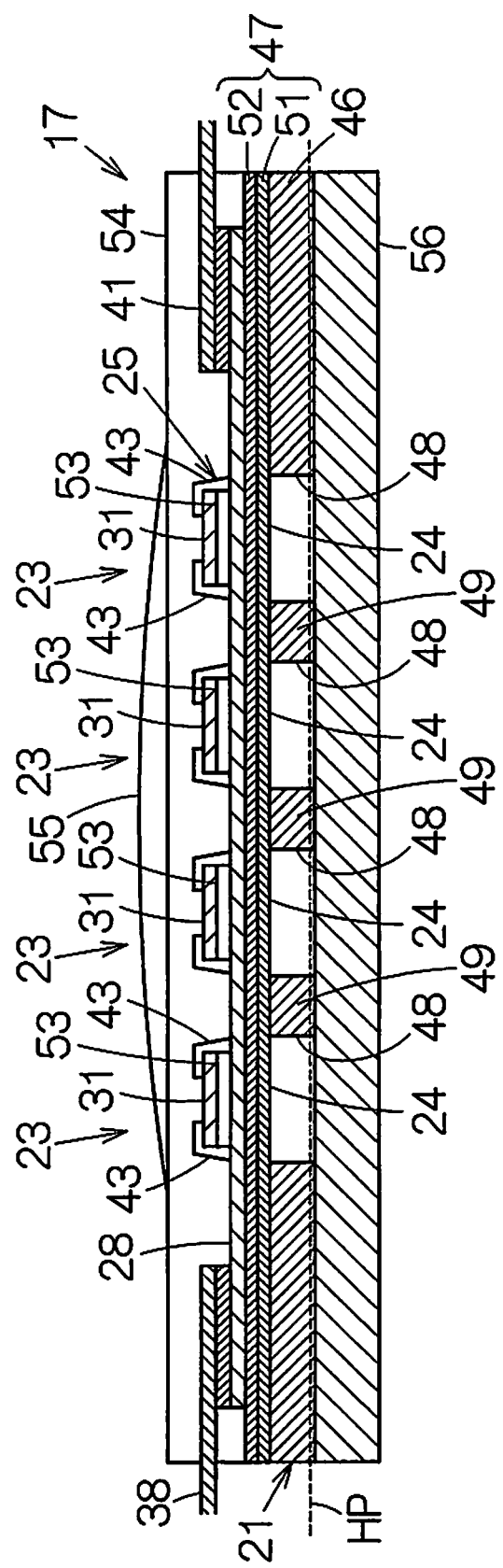
FIG. 4 is a cross section view along line A-A of FIG. 3.

As shown in FIG. 4, the base 21 is equipped with a main unit 46 and a flexible film 47. The flexible film 47 is formed over the entire surface on the surface of the main unit 46. The main unit 46 is formed from silicon (Si), for example. An opening 48 is formed on each individual element 23 on the main unit 46. The openings 48 are arranged in array form on the main unit 46. The outline of the area in which the openings 48 are arranged correlates to the outline of the element array 22. A partition wall 49 is demarcated between two adjacent openings 48. Adjacent openings 48 are partitioned by the partition wall 49. The wall thickness of the partition wall 49 correlates to the gap between the openings 48. The partition wall 49 defines two wall surfaces within the plane mutually expanding in parallel. The wall thickness correlates to the distance between two wall surfaces. Specifically, the wall thickness can be regulated by the length of the perpendicular line sandwiched between the wall surfaces orthogonal to the wall surface.

The flexible film 47 is constituted by a silicon oxide ($SiO_2$) layer 51 laminated on the surface of the main unit 46, and a zirconium oxide ($ZrO_2$) layer 52 laminated on the surface of the silicon oxide layer 51. The flexible film 47 is in contact with the opening 48. In this way, a portion of the flexible film 47 corresponding to the outline of the opening 48 forms the vibration film 24. Of the flexible film 47, the vibration film 24 is the part for which it is possible to do film vibration in the thickness direction of the main unit 46 since it faces the opening 48. The film thickness of the silicon oxide layer 51 can be determined based on the resonance frequency.

On the surface of the vibration film 24 are laminated in sequence the first conductor 28, the piezoelectric film 53, and the second conductor 31. The piezoelectric film 53 can be formed using lead zircon titanate (PZT), for example. It is also possible to use another piezoelectric material for the piezoelectric film 53. The piezoelectric film 53 covers at least a portion of the lower electrode 27 and a portion of the vibration film 24. The upper electrode 26 covers at least a portion of the piezoelectric film 53. Here, the piezoelectric film 53 completely covers the surface of the first conductor 28 below the second conductor 31. It is possible to avoid shorting between the first conductor 28 and the second conductor 31 by working of the piezoelectric film 53.

As shown in FIG. 4, the electrode separation film 43 covers the side surface of the piezoelectric element 25. Specifically, the electrode separation film 43 is formed on the piezoelectric film 53 between the first conductor 28 and the second conductor 31. In this way, the surface of the piezoelectric film 53 between the first conductor 28 and the second conductor 31 is covered by the electrode separation film 43. Here, the electrode separation film 43 stays inside the area of the vibration film 24 in the lengthwise direction of the first conductor 28. The electrode separation film 43 does not touch the edge of the vibration film 24.

An acoustic adjustment layer 54 is laminated on the surface of the base 21. The acoustic adjustment layer 54 can be cover the surface of the base 21 over the entire surface, for example. As a result, the element array 22, the first and second terminal arrays 33a and 33b, and the first and second wiring boards 38 and 41 are covered by the acoustic adjustment layer 54. The acoustic adjustment layer 54 is adhered to the surface of the element 23. It is possible to use a silicone resin film for the acoustic adjustment layer 54, for example. The acoustic adjustment layer 54 protects the element array 22 structure, the first terminal array 33a and the first wiring board 38 junction, and the second terminal array 33b and the second wiring board 41 junction.

An acoustic lens 55 is laminated on the acoustic adjustment layer 54. The acoustic lens 55 is adhered to the surface of the acoustic adjustment layer 54. The outer surface of the acoustic lens 55 is formed with a partial cylindrical surface. The partial cylindrical surface has a generatrix parallel to the second conductor 31. The curvature of the partial cylindrical surface is determined according to the focal position of the ultrasonic waves emitted from one row of elements 23 connected to one line of the first conductors 28. The acoustic lens 55 is formed from silicone resin, for example.

A reinforcing plate 56 is fixed to the hack surface of the base 21. The back surface of the base 21 is overlapped on the front surface of the reinforcing plate 56. The reinforcing plate 56 closes the openings 48 at the back surface of the element unit 17. The reinforcing plate 56 can be equipped with a rigid base. The reinforcing plate 56 can be formed from a silicon substrate, for example. The plate thickness of the base 21 is set to approximately 100 μm, for example, and the plate thickness of the reinforcing plate 56 is set to approximately 100 to 150 μm, for example. Here, the partition wall 49 is bonded to the reinforcing plate 56. The reinforcing plate 56 is bonded at a bonding area of at least one location on each partition wall 49. An adhesive agent can be used for the bonding.

Figure 5:
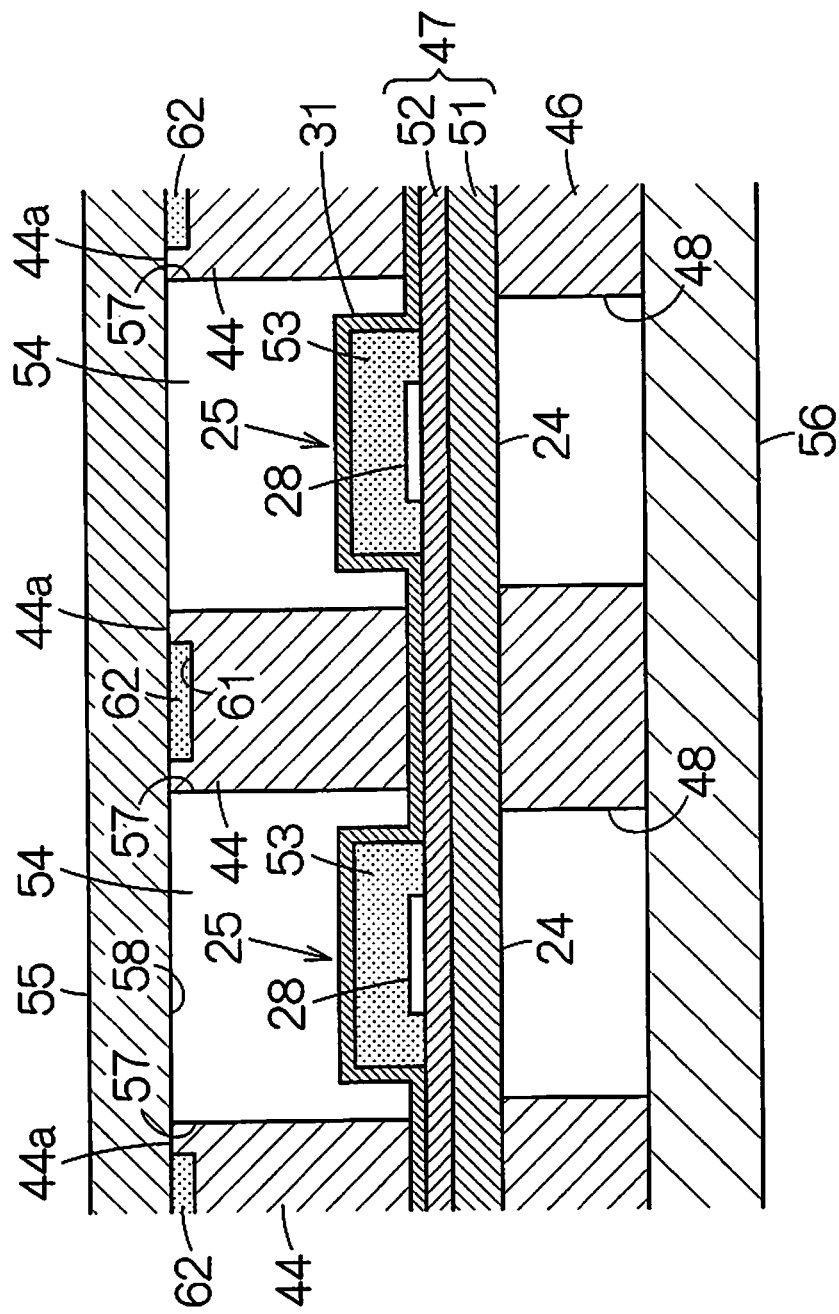
FIG. 5 is a cross section view along line B-B of FIG. 3.

As shown in FIG. 5, the piezoelectric film 53 is covered on the first conductor 28. The piezoelectric film 53 contacts the surface of the vibration film 24 in a range expanding to the outside from the edge of the first conductor 28. The piezoelectric film 53 completely separates the first conductor 28 and the second conductor 31 from each other. This avoids a short between the first conductor 28 and the second conductor 31.

As shown in FIG. 5, parts of the adjacent acoustic adjustment layer 54 are separated from each other by a separation space 57. The separation space 57 is occupied by the separating wall 44. The separating wall 44 is formed using an object having acoustic impedance greater than the acoustic impedance of the acoustic adjustment layer 54. The separating wall 44 is constituted from a solid having a Young's modulus greater than the Young's modulus of the acoustic adjustment layer 54.

The acoustic lens 55 has a bonding surface 58 that expands within one plane. The acoustic lens 55 is adhered to the acoustic adjustment layer 54 and the top surface 44a of the separating wall 44 without interruption at the bonding surface 58. A cavity 61 that is recessed from the bonding surface with the acoustic lens 55 is formed on the top surface 44a of the separating wall 44. The space inside the cavity 61 is occupied by an adhesive layer 62. The top surface 44a of the separating wall 44 is bonded to the acoustic lens 55 by the adhesive layer 62. The adhesive layer 62 is formed using the same material as the acoustic adjustment layer 54.

(2) Operation of the Ultrasonic Diagnostic Device

Next, a brief description of the operation of the ultrasonic diagnostic device 11 will be provided. For sending of ultrasonic waves, pulse signals are supplied to the piezoelectric element 25. The pulse signals are supplied to the elements 23 for each row through the lower electrode terminals 35 and 37 and the upper electrode terminals 34 and 36. With each element 23, an electric field acts on the piezoelectric film 53 between the lower electrode 27 and the upper electrode 26. The piezoelectric film 52 vibrates with the ultrasonic waves. The vibration of the piezoelectric film 52 is conveyed to the vibration film 24. In this way, the vibration film 24 does ultrasonic vibration. As a result, the desired ultrasonic beams are emitted toward the subject (e.g. the interior of a human body).

The reflected waves of the ultrasonic waves vibrate the vibration film 24. The ultrasonic vibration of the vibration film 24 makes the piezoelectric film 53 do ultrasonic vibration at a desired frequency. Voltage is output from the piezoelectric element 25 according to the piezoelectric effect of the piezoelectric element 25. Electric potential is generated between the upper electrode 26 and the lower electrode 27 with each element 23. The electric potential is output as electric signals from the lower electrode terminals 35 and 37 and the upper electrode terminals 34 and 36. In this way, ultrasonic waves are detected.

The sending and receiving of ultrasonic waves is repeated. As a result, linear scanning or sector scanning is realized. When scanning is completed, an image is formed based on the digital signals of the output signals. The formed image is displayed on the screen of the display panel 15.

The vibration film 24 does ultrasonic vibration with the sending of ultrasonic waves. The ultrasonic vibration is transmitted within the acoustic adjustment layer 54, and emitted from the interface of the acoustic adjustment layer 54. The ultrasonic vibration is transmitted across the interface to the acoustic lens 55. At this time, the separation space 57 between adjacent elements 23 is defined, and that separation space 57 is occupied by an object with a large acoustic impedance, specifically, the separating wall 44. In this way, an interface is formed on the acoustic adjustment layer 54 between adjacent elements 23 according to the difference in acoustic impedance. The interface prevents transmission of the ultrasonic vibration. As a result, the transmission of ultrasonic vibration from one vibration film 24 that does ultrasonic vibration toward the vibration film 24 of the adjacent element 23 is prevented. Ultrasonic wave crosstalk during ultrasonic vibration of one vibration film 24 is prevented. If the separating wall 44 is not formed and the acoustic adjustment layer 54 expands in common between elements 23 with each other, the ultrasonic vibration emitted from one element 23 is reflected from the interface of the acoustic adjustment layer 54 and the acoustic lens 55 and is propagated in the vibration film 24 of other elements 23.

With the element unit 17, segments are formed for each element 23 group connected in common to one signal line, specifically, one line of the first conductors 28. The vibration films 24 belonging to one segment vibrate simultaneously according to the supply of drive signals. There are cases when the operating timing differs between one segment and another segment with implementation of linear scanning or sector scanning. At this time, the separating wall 44 separates the acoustic adjustment layer 54 for each segment. Therefore, transmission of ultrasonic vibration from the vibration films 24 belonging to one segment toward the vibration films 24 belonging to another segment is prevented. Crosstalk is prevented.

As described previously, the separating wall 44 is constituted using a solid having a Young's modulus greater than the Young's modulus of the acoustic adjustment layer 54. As a result, the rigidity of the acoustic adjustment layer 54 is reinforced by the separating wall 44. Crushing of the acoustic adjustment layer 54 in the thickness direction is prevented. The distance between the vibration film 24 and the interface of the acoustic adjustment layer 54 is kept constant. Ultrasonic waves can be radiated from the interface efficiently. At this time, the acoustic lens 55 is adhered to the surface of the acoustic adjustment layer 54 and the top surface 44a of the separating wall 44 by the bonding surface 58. Therefore, the acoustic lens 55 is supported by the separating wall 44. It is possible to reliably prevent crushing of the acoustic adjustment layer 54 in the thickness direction.

The surface of the acoustic adjustment layer 54 has the function of an adhesive agent. As a result, the acoustic lens 55 is adhered to the acoustic adjustment layer 54. Close adherence is maintained. Though the surface of the acoustic adjustment layer 54 is interrupted by the separation space 57, the acoustic lens 55 is adhered to the top surface 44a of the separating wall 44 by the work of the adhesive layers 62. Even when the separation space 57 is formed, a reduction in the acoustic lens 55 adherence area is kept to a minimum. In fact, when the acoustic lens 55 is bonded to the separating wall 44, it is possible for the acoustic lens 55 and the separating wall 44 to form a structure. The structure can even more reliably prevent deformation of the acoustic adjustment layer 54.

The cavity 61 is formed on the top surface 44a of the separating wall 44. The cavity 61 is occupied by the adhesive layer 62. The acoustic lens 55 is bonded to the top surface 44a of the separating wall 44 by the adhesive layer 62. At this time, the acoustic lens 55 is received on the top surface 44a of the separating wall 44. Therefore, the thickness of the acoustic adjustment layer 54 is determined by the position of the top surface 44a of the separating wall 44. The thickness of the acoustic adjustment layer 54 can be set with good precision according to the dimensional precision of the separating wall 44. In fact, the reduction in the adherence area of the acoustic lens 55 is kept to a minimum.

With the element unit 17, the adhesive layer 62 is formed using the same material as the acoustic adjustment layer 54. Therefore, as described later, the adhesive layer 62 can be formed using the same manufacturing process as that of the acoustic adjustment layer 54. Having the manufacturing process become complex is avoided. Having the manufacturing cost increase is avoided.

(3) Element Unit of the Second Embodiment

Figure 6:
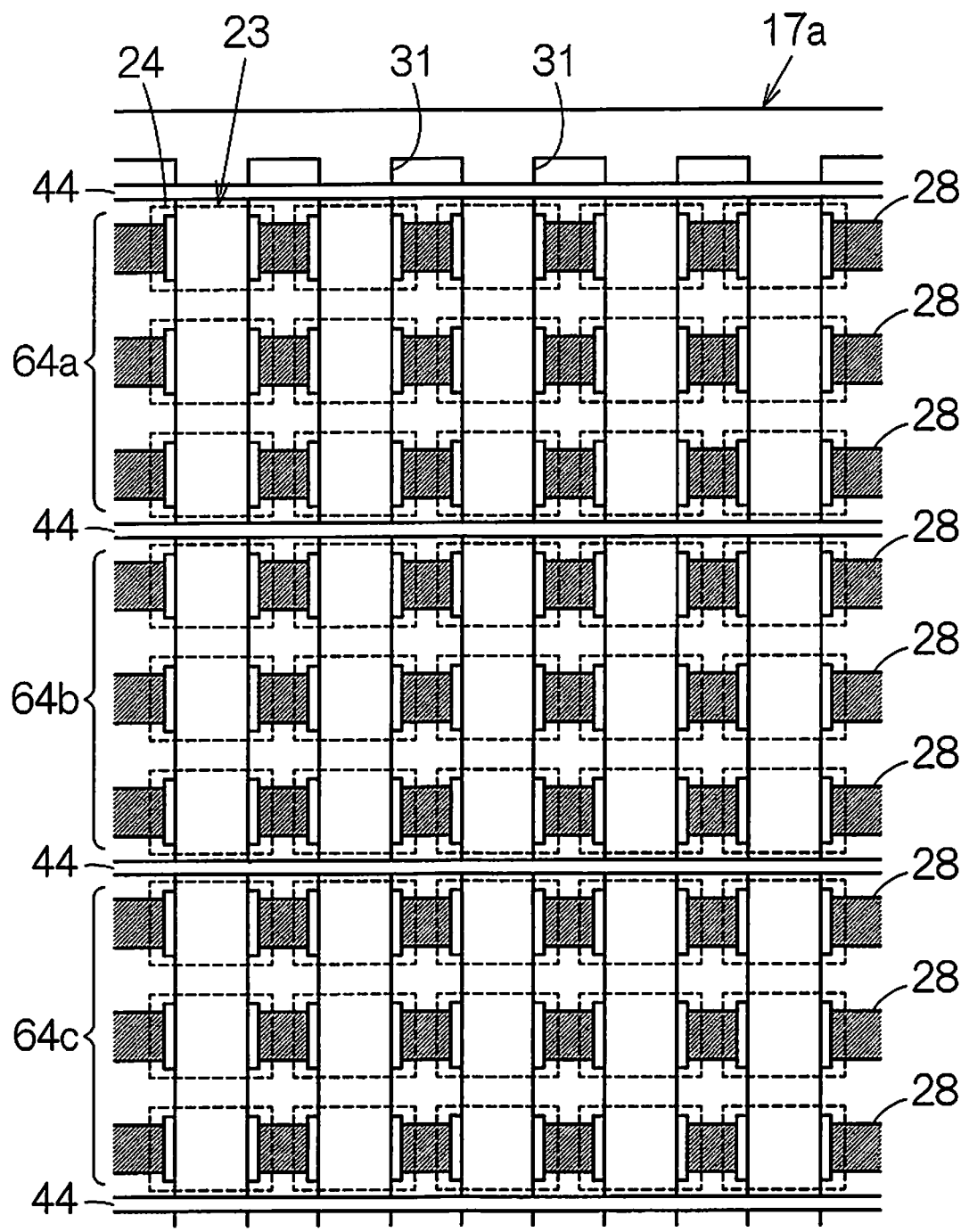
FIG. 6 is an enlarged partial plan view of the ultrasonic transducer element unit of the second embodiment, correlating to a partial enlarged view of FIG. 3.

FIG. 6 schematically shows the structure of an element unit 17a of the second embodiment. With this element unit 17a, one segment 64a, 64b, 64c, . . . is formed from a group of a plurality of rows of elements 23. In the drawing, one segment 64a, 64b, and 64c is formed from the element 23 group connected in common to three lines of the first conductors 28. The vibration films 24 belonging to one segment 64a, 64b, and 64c vibrate simultaneously according to the supply of drive signals. The separating wall 44 is arranged mutually between the segments 64a, 64b, and 64c. The separating wall 44 segments the element array 22 for each segment 64a, 64b, and 64c. In this way, when the groups of elements 23 of the plurality of rows do ultrasonic vibration simultaneously, it is possible to increase the strength of the ultrasonic waves. The separating wall 44 separates the acoustic adjustment layer 54 for each segment 64a, 64b, and 64c. Therefore, transmission of the ultrasonic vibration from the vibration films 24 belonging to one segment 64a (64b) (64c) toward the vibration films 24 belonging to other segments 64b, 64c (64a, 64c) (64a, 64b) is prevented. Crosstalk is prevented. In addition, the constitution other than the constitution mentioned with the description above is the same as that of the element unit 17 of the first embodiment described previously.

(4) Element Unit of the Third Embodiment

Figure 7:
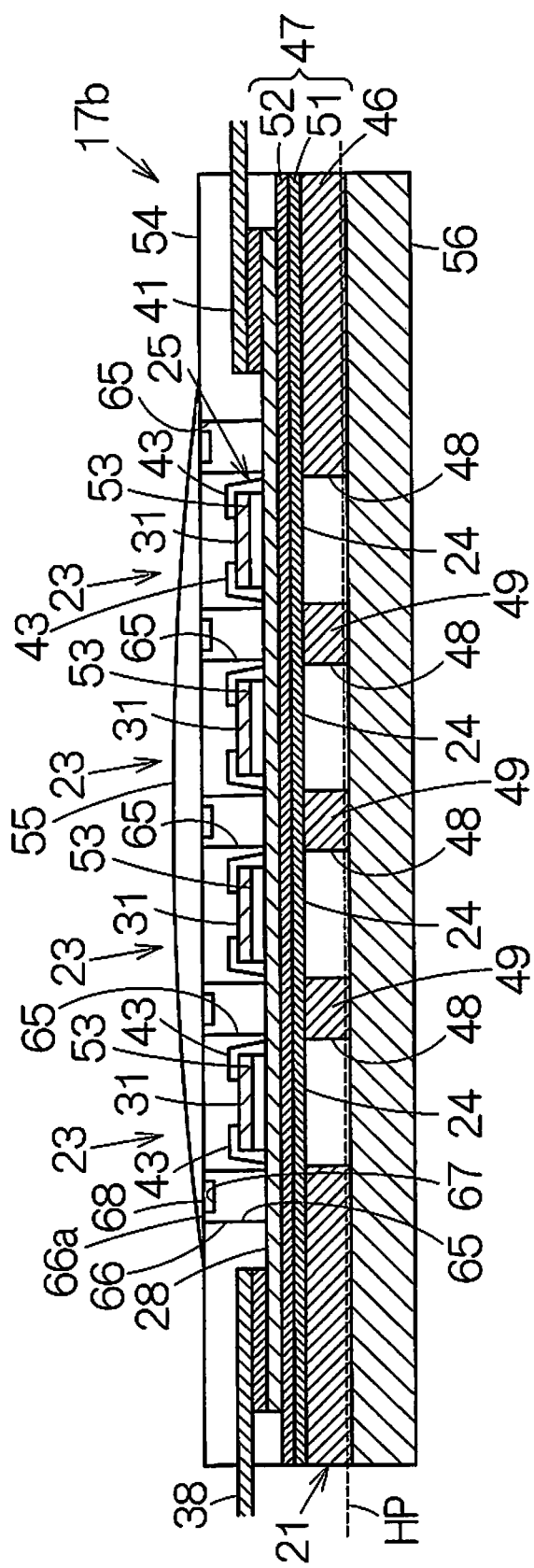
FIG. 7 is a cross section view of the ultrasonic transducer element unit of the third embodiment, corresponding to FIG. 4.

FIG. 7 schematically shows the structure of an element unit 17b of the third embodiment. With this element unit 17b, in addition to the previously described separation space 57 that divides the acoustic adjustment layer 54 for each segment, a separation space 65 is formed that further separates the acoustic adjustment layer 54 within the segment. The separation space 65 extends in the lengthwise direction of the second conductor 31, and segments of the acoustic adjustment layer 54 on adjacent elements 23 in the group of elements 23 connected in common to one signal line are separated from each other. The separation space 65 is occupied by a separating wall 66. The separating wall 66, the same as with the separating wall 44, is formed using an object having higher acoustic impedance than the acoustic impedance of the acoustic adjustment layer 54. The separating wall 66 is constituted from a solid having a Young's modulus greater than the Young's modulus of the acoustic adjustment layer 54. In this way, the transmission of ultrasonic vibration between vibration films 24 vibrating simultaneously is prevented. Crosstalk of the ultrasonic waves between vibration films 24 vibrating simultaneously with each other is prevented. In addition, the constitution other than the constitution mentioned with the description above is the same as that of the element units 17 and 17a of the first embodiment or second embodiment described previously.

Here, the separating wall 66 can be formed in the same manner as the separating wall 44 described previously. Specifically, the acoustic lens 55 is adhered without interruption to the acoustic adjustment layer 54 and a top surface 66a of the separating wall 66 by the bonding surface 58. A cavity 67 recessed from the bonding surface with the acoustic lens 55 is formed on the top surface 66a of the separating wall 66. The space inside the cavity 67 is occupied by an adhesive layer 68. The top surface 66a of the separating wall 66 is bonded to the acoustic lens 55 by the adhesive layer 68. The adhesive layer 68 is formed using the same material as that of the acoustic adjustment layer 54.

(5) Manufacturing Method of the Element Unit

Figure 8:
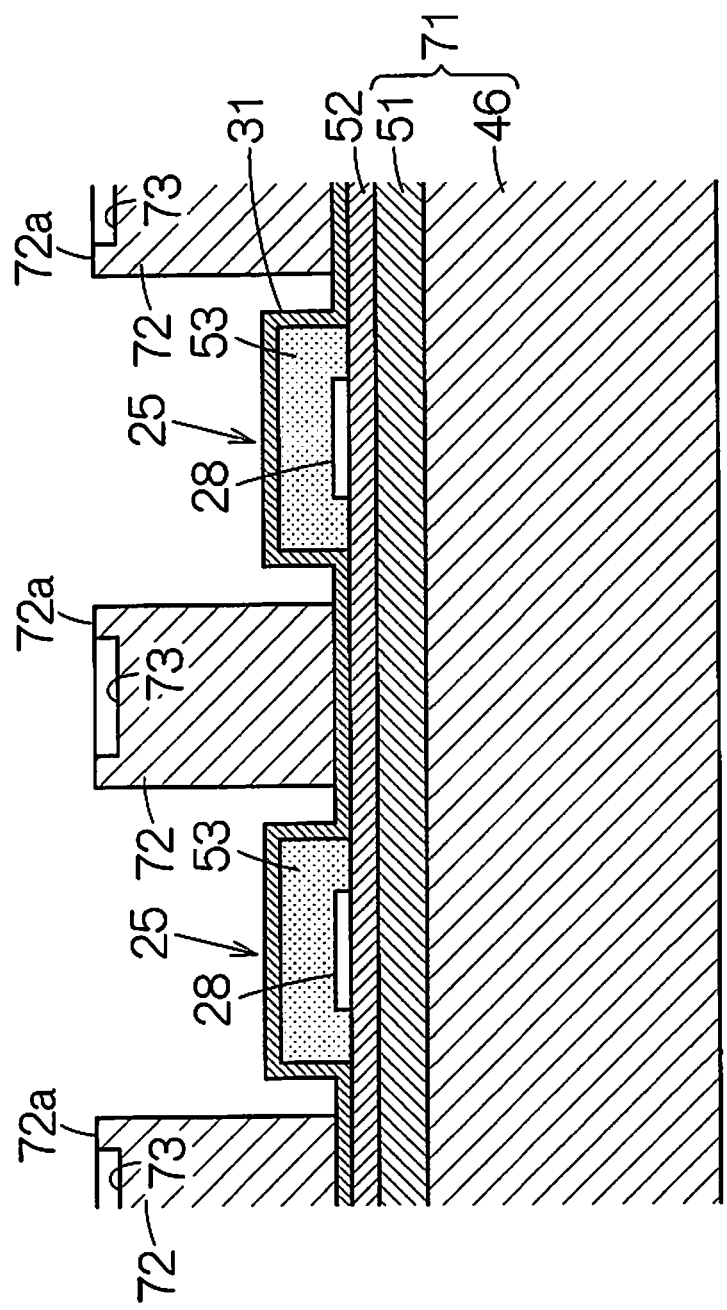
FIG. 8 is a drawing schematically showing the wall body forming process, which is part of the manufacturing method of the ultrasonic transducer element unit.

Here, a brief description of the method of manufacturing the element unit 17 (17a, 17b) will be provided. A substrate 71 is prepared. The substrate 71 is formed from silicon, for example. On the surface of the substrate 71, for example, a heat treatment is implemented and an oxide film is formed. In this way, the main unit 46 and the silicon oxide layer 51 are formed from the substrate 71. On the surface of the silicon oxide layer 51, the zirconium oxide layer 52 is formed on the entire surface. After that, as shown in FIG. 8, on the surface of the zirconium oxide layer 52 are formed an element array 22 containing piezoelectric elements 25, first and second conductors 28 and 31, first and second terminal arrays 33a and 33b and the like. Photolithography technology can be used for forming these.

A wall body 72 is formed between piezoelectric elements 25 on the surface of the zirconium oxide layer 52. Photolithography technology, for example, can be used for forming the wall body 72. When forming the wall body 72 itself using a photoresist material, the photoresist film modeling the shape of the separating wall 44 can be allowed to remain after exposure. When the wall body 72 is formed using a material other than a photoresist material, it is possible for the space in which the shape of the separating wall 44 is modeled to be demarcated using a photoresist film after exposure.

Figure 9:
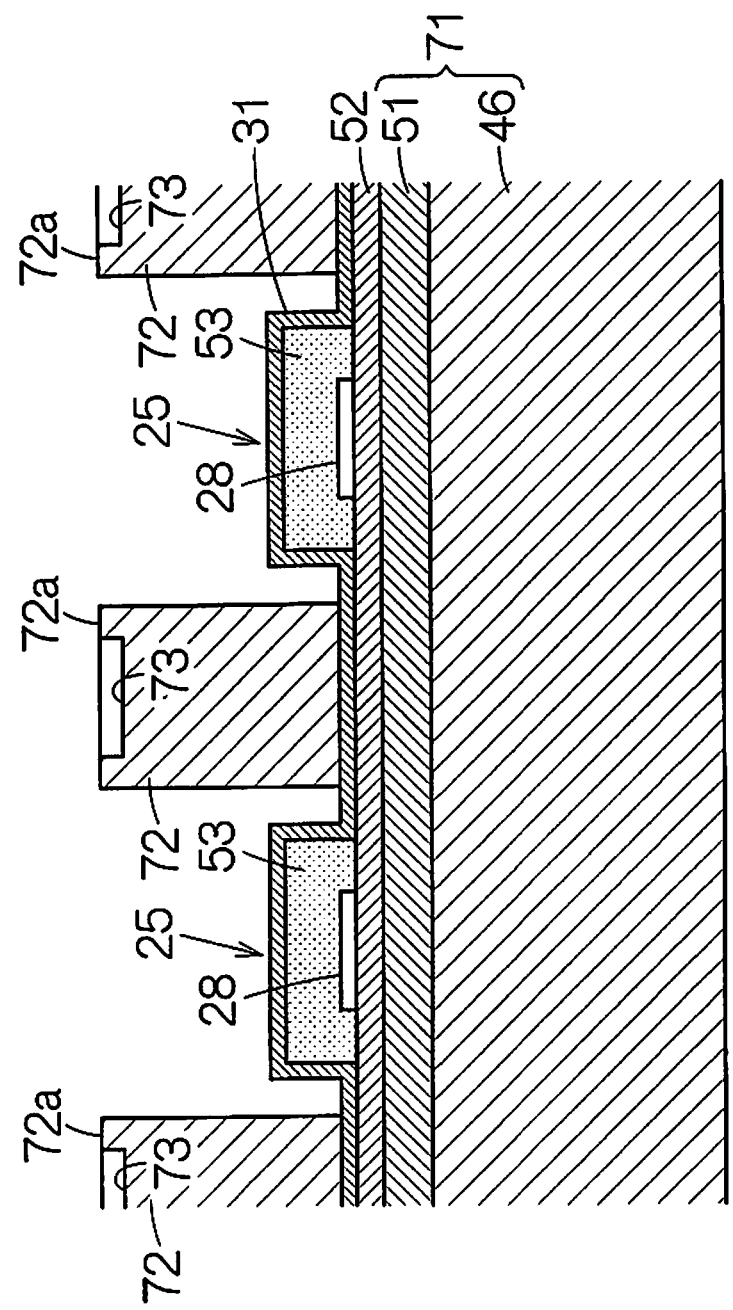
FIG. 9 is a drawing schematically showing the cavity forming process which is part of the manufacturing method of the ultrasonic transducer element unit.

Subsequently, as shown in FIG. 9, a cavity 73 is formed on a top surface 72a of the wall body 72. Photolithography technology, for example, can be used for forming the cavity 73. The top surface 72a can be exposed in the etching process, for example, after being protected by the photoresist film. After that, unnecessary photoresist film is removed. Here, the silicon oxide layer 51 is left remaining and openings 48 are drilled from the back surface of the substrate 71, and the reinforcing plate 56 is bonded to the back surface of the substrate 71. However, the bonding of the opening 48 and the reinforcing plate 56 can be implemented following completion of the piezoelectric elements 25.

Figure 10:
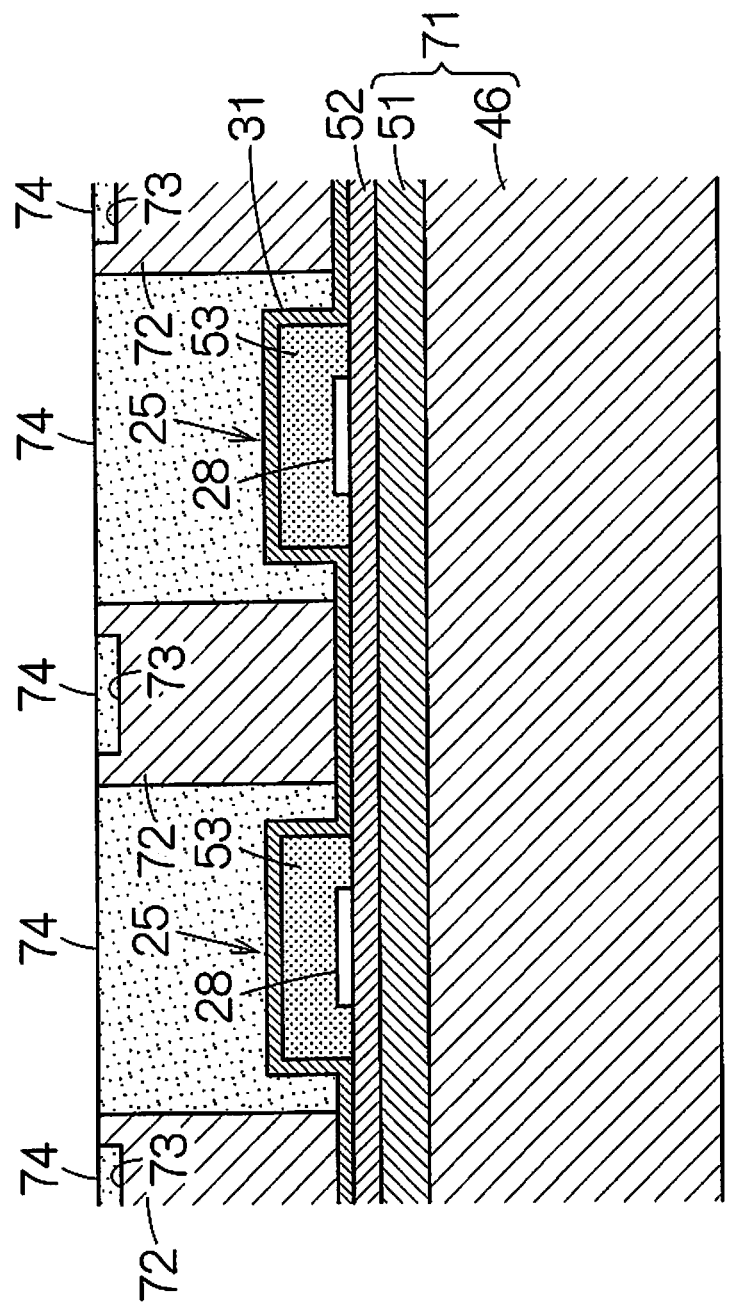
FIG. 10 is a drawing schematically showing the acoustic adjustment layer and adhesive layer forming process which is part of the manufacturing method of the ultrasonic transducer element unit.

As shown in FIG. 10, the material of the acoustic adjustment layer 54 flows onto the surface of the zirconium oxide layer 52. The material 74 of the acoustic adjustment layer 54 has fluidity, for example. The material 74 embeds the space between the wall bodies 72. Simultaneously, the material 74 embeds the space of the cavity 73. The surface of the material 74 is preferably the entire surface of the top surface 72a of the wall body 72. The material 74 is hardened. As a result, the acoustic adjustment layer 54 and the adhesive layer 62 are established.

After that, the acoustic lens 55 is overlapped on the surface of the acoustic adjustment layer 54. The acoustic lens 55 is adhered to the acoustic adjustment layer 54 and the adhesive layer 62 by the bonding surface 58. Since the acoustic adjustment layer 54 and the adhesive layer 62 have the function of an adhesive agent, the adhesion of the acoustic adjustment layer 54 and the adhesive layer 62 with the acoustic lens 55 continues to be maintained. In this way, since the acoustic adjustment layer 54 and the adhesive layer 62 are formed using the same material, it is possible to form the adhesive layer 62 using the same manufacturing process as the acoustic adjustment layer 54. As a result, having the manufacturing process become more complex is avoided. An increase in manufacturing costs is avoided.

A detailed description of the embodiments was given as noted above, but a person skilled in the art will easily understand that it is possible to have many modifications without substantially straying from the novel items and effects of the present invention. Therefore, all of these kinds of modification examples are included within the scope of the present invention. For example, for terminology noted at least once together with a different term having a broader or the same meaning in the specification or drawings, that different terminology can be used as a substitute in any location in the specification or drawings. Also, the constitution and operation of the ultrasonic diagnostic device 11, the ultrasonic probe 13, the element units 17, 17a, and 17b, the elements 23, the piezoelectric elements 25 and the like are not limited to the items described with the embodiments, but can also have various modifications. As long as the functions and effects are exhibited as anticipated, the height of the separating wall 44 can be lower than the height of the acoustic adjustment layer 54 as well.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic device comprising:
a base including a main body and a flexible film;
a plurality of ultrasonic transducer elements arranged in an array form on the base, each of the ultrasonic transducer elements having a vibration film;
an acoustic adjustment layer disposed on each of the ultrasonic transducer elements; and a wall part arranged between adjacent ones of the ultrasonic transducer elements when viewed in a plane view along a thickness direction of the base, the wall part comprising a material separates the acoustic adjustment layer on the adjacent ones of the ultrasonic transducer elements in a range of at least a portion of a height of the acoustic adjustment layer measured from the base, and the material having an acoustic impedance that is higher than an acoustic impedance of the acoustic adjustment layer; and an acoustic lens adhered to the acoustic adjustment layer, the acoustic lens being bonded to a top surface of the wall part using an adhesive layer, the main body having an opening in a position corresponding to each of the ultrasonic transducer elements, the vibration film being a part of the flexible film, the vibration film facing the opening and being configured to vibrate in the thickness direction of the base, the wall part being disposed outside an area in which the vibration film is located on the base, and the wall part having a cavity recessed forming a bonding surface with the acoustic lens, and the cavity is filled with the adhesive layer.

2. The ultrasonic device according to claim 1, wherein the wall part is made of a material having larger Young's modulus than Young's modulus of a material of the acoustic adjustment layer.

3. The ultrasonic device according to claim 1, wherein the adhesive layer is made of the same material as the acoustic adjustment layer.

4. The ultrasonic device according to claim 1, wherein the wall part separates the acoustic adjustment layer for each of an ultrasonic transducer element group including the ultrasonic transducer elements connected in common to one signal line among the ultrasonic transducer elements.

5. The ultrasonic device according to claim 4, wherein the wall part separates the acoustic adjustment layer on the adjacent ones of the ultrasonic transducer elements within the ultrasonic transducer element group.

6. A probe comprising:
the ultrasonic device according to claim 1; and
a case supporting the ultrasonic device.

7. An electronic equipment comprising:
the ultrasonic device according to claim 1; and
a processing device connected to the ultrasonic device, and configured to process output of the ultrasonic device.

8. An ultrasonic image device comprising:
the ultrasonic device according to claim 1; and
a display device configured to display an image generated based on output of the ultrasonic device.

* * * * *